(12) United States Patent
Lu

(10) Patent No.: US 11,032,633 B2
(45) Date of Patent: Jun. 8, 2021

(54) METHOD OF ADJUSTING TONE AND TONE-ADJUSTABLE EARPHONE

(71) Applicant: Tymphany Acoustic Technology Limited, Taipei (CN)

(72) Inventor: Ryan Meng-Wei Lu, Taipei (TW)

(73) Assignee: TYMPHANY ACOUSTIC TECHNOLOGY LIMITED, Taipei (TW)

( * ) Notice: Subject to any disclaimer, the term of this patent is extended or adjusted under 35 U.S.C. 154(b) by 0 days.

(21) Appl. No.: 17/004,836

(22) Filed: Aug. 27, 2020

(65) Prior Publication Data
US 2021/0067860 A1    Mar. 4, 2021

(30) Foreign Application Priority Data

Sep. 3, 2019   (CN) .......................... 201910827569.8

(51) Int. Cl.
| | |
|---|---|
| *H04R 1/10* | (2006.01) |
| *H04R 1/08* | (2006.01) |
| *A61B 5/107* | (2006.01) |
| *A61B 5/00* | (2006.01) |
| *H04R 29/00* | (2006.01) |

(52) U.S. Cl.
CPC .......... *H04R 1/1041* (2013.01); *A61B 5/1073* (2013.01); *A61B 5/4872* (2013.01); *H04R 1/08* (2013.01); *H04R 1/1075* (2013.01); *H04R 29/001* (2013.01); *A61B 2503/12* (2013.01)

(58) Field of Classification Search
CPC ...... H04R 1/1041; H04R 1/08; H04R 1/1075; H04R 29/001; A61B 5/1073; A61B 5/4872; A61B 2503/12
See application file for complete search history.

(56) References Cited

U.S. PATENT DOCUMENTS

2017/0105083 A1 *   4/2017   Nair .......................... H04S 7/30

* cited by examiner

*Primary Examiner* — Andrew L Sniezek
(74) *Attorney, Agent, or Firm* — Muncy, Geissler, Olds & Lowe, P.C.

(57) ABSTRACT

A method of adjusting a tone and a tone-adjustable earphone includes obtaining bioinformation of the user, wherein the bioinformation includes a head volume, calculating a nature frequency of the head of the user according to the bioinformation and adjusting a playback tone of the earphone according to the nature frequency of the head.

9 Claims, 2 Drawing Sheets obtaining bioinformation of a user — 101 calculating an nature frequency of the user according to the bioinformation — 102 adjusting a playback tone of the earphone according to the nature — 103

METHOD OF ADJUSTING TONE AND TONE-ADJUSTABLE EARPHONE

CROSS REFERENCE TO RELATED APPLICATIONS

The present application claims priority to Chinese Patent Application No. CN 201910827569.8, which was filed on Sep. 3, 2019 the entire contents of which are hereby incorporated by reference.

BACKGROUND OF THE INVENTION

Technical Field

The present application relates to a method of adjusting a tone and a tone-adjustable earphone, in particular to a tone-adjustable earphone and a method of adjusting a tone according to a nature frequency of a user.

Related Art

Earphones have been developed for many years, and each manufacturer has continually researched and developed various kinds of methods for adjusting a tone to provide a better listening experience for users.

Each part of a human body, especially the head, has a nature frequency. Since each user has a different nature frequency, the same sound transmitted to the ears of different people may cause different experiences.

At present, traditional earphones do not consider different nature frequencies of the users, and the heard sound (music) cannot be adjusted according to the body differences of each person. If the tone can be tuned according to the nature frequency of each user, the earphone user (listener) will have richer acoustic enjoyment.

SUMMARY

The present application provides a method of adjusting a tone. The method includes obtaining bioinformation of the user, wherein the bioinformation includes a head volume; calculating a nature frequency of the head of the user according to the bioinformation; and adjusting a playback tone of the earphone according to the nature frequency of the head.

In exemplary embodiments, the head volume of the user is obtained by utilizing a speaker driver and a microphone. The speaker driver and the microphone are respectively located at two ears of the earphone. The speaker driver provides a pulse signal. The microphone receives the pulse signal. A head width of the user is obtained by utilizing a time difference between the pulse signal provided by the speaker driver and the pulse signal received by the microphone. A head area of the user is obtained by utilizing an intensity attenuation difference between the pulse signal provided by the speaker driver and the pulse signal received by the microphone. The head volume of the user is capable of being obtained according to the head width of the user and the head area of the user. More preferably, the head area of the user is obtained according to the intensity attenuation difference between the pulse signal provided by the speaker driver and the pulse signal received by the microphone. The intensity attenuation difference is based on an acoustic shadow effect of the user.

In exemplary embodiments, the bioinformation includes a body fat rate, and a head density and a head weight of the user are capable of being obtained according to the body fat rate and the head volume.

In exemplary embodiments, the bioinformation includes a heart rate or a perspiration rate, and the head density and the head weight of the user are capable of being obtained according to the heart rate or the perspiration rate and the head volume.

The present application further provides a tone-adjustable earphone. A user wears the earphone. The earphone includes a first housing comprising a speaker driver; a second housing comprising a microphone, wherein the speaker driver provides a pulse signal, and the microphone receives the pulse signal; and a processor electrically connected with the speaker driver and the microphone. The processor calculates a head volume of the user according to a time difference between the pulse signal provided by the speaker driver and the pulse signal received by the microphone and according to an intensity attenuation difference between the pulse signal provided by the speaker driver and the pulse signal received by the microphone. The processor calculates a nature frequency of the head of the user according to a body fat rate and the head volume of the user, and according to the nature frequency of the head, the processor controls to adjust a playback tone of the earphone.

The present application further provides another tone-adjustable earphone. The earphone is capable of being communicated with a mobile phone. The mobile phone is capable of controlling to adjust a playback tone of the earphone. A user wears the earphone, and the mobile phone stores bioinformation of the user. The earphone includes a first housing comprising a speaker driver; and a second housing comprising a microphone. The speaker driver provides a pulse signal, and the microphone receives the pulse signal. The mobile phone calculates a head volume of the user according to a time difference between the pulse signal provided by the speaker driver and the pulse signal received by the microphone and according to an intensity attenuation difference between the pulse signal provided by the speaker driver and the pulse signal received by the microphone. The bioinformation of the user includes a body fat rate. The mobile phone calculates a nature frequency of the head of the user according to the head volume and the body fat rate, and according to the nature frequency of the head, the mobile phone controls to adjust a playback tone of the earphone.

According to an earphone of an exemplary embodiment, a head area of the user is capable of being calculated according to the intensity attenuation difference between the pulse signal provided by the speaker driver and the pulse signal received by the microphone. The intensity attenuation difference is based on an acoustic shadow effect of the user.

According to an earphone of an exemplary embodiment, the bioinformation includes a heart rate or a perspiration rate. The mobile phone is capable of calculating a head density and a head weight of the user according to the heart rate or the perspiration rate and the head volume.

Based on the above, according to the present application, after the nature frequency is obtained, the playback tone of the earphone is capable of being controlled to be adjusted. That is, adjusting is performed according to the nature frequency. A parameter equalizer (PEQ) may be accompanied for adjusting tone calibration or enhancement.

DETAILED DESCRIPTION

To fully understand the objectives, features, and effects of the present application, the following describes the present application in detail with reference to specific embodiments and accompanying drawings. The description is as follows.

Figure 1:
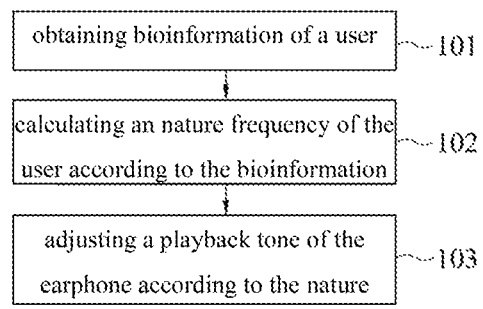
FIG. 1 is a flow diagram according to a method of adjusting a tone of the present application.

The present application provides a method of adjusting a tone. The method provides tonal calibration when a user wears an earphone. Referring to a flow diagram in FIG. 1, Step 101: obtaining the user's bioinformation. The bioinformation includes a head volume of the user. Step 102: calculating for a nature frequency of the user's head according to the bioinformation. Step 103: adjusting a tone for the earphone playing according to the nature frequency of the user's head.

Figure 2:
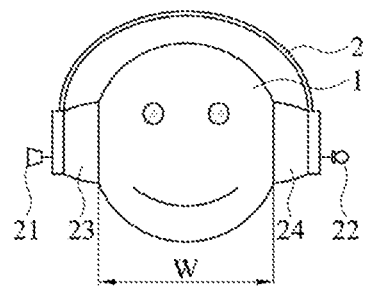
FIG. 2 is a use state diagram according to one embodiment of an earphone of the present application.
Figure 3:
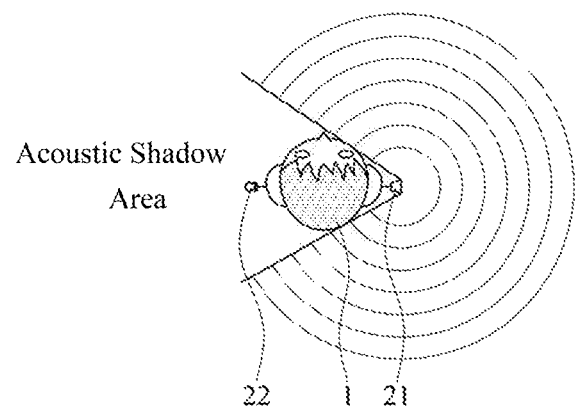
FIG. 3 is measurement of a head volume of a user according to the use of FIG. 2.

Further, the obtained bioinformation of the user may be input by the user himself or herself. For example, the user 1 may input his/her head width, length, and depth so as to obtain the head volume. Referring to FIG. 2, the head volume of the user 1 can be obtained by utilizing a speaker driver 21 and a microphone 22. As shown in FIG. 2, the speaker driver 21 and the microphone 22 are respectively located at two ears of the earphone 2. The speaker driver 21 provides a pulse signal, and the microphone 22 receives the pulse signal. A head width W of the user 1 can be obtained by calculating time difference between the pulse signal provided by the speaker driver and the pulse signal received by the microphone. A head area of the user 1 can be obtained by analyzing an intensity attenuation difference between the pulse signal provided by the speaker driver and the pulse signal received by the microphone. FIG. 3 shows an acoustic shadow effect. The acoustic shadow effect is caused by the area formed by head height and head depth blocking higher frequency acoustic waves. The larger the area, the more difference there is in intensity of higher frequencies. Acoustic waves shown in FIG. 3 are in an X-Y plane and have an acoustic shadow area caused by the head of the user 1 blocking. The intensity attenuation difference between the pulse signal provided by the speaker driver 21 and the pulse signal received by the microphone 22 may be calculated. The head area of the user 1 is obtained in an X direction (vertical direction) and in a Z direction (direction penetrating the figure). After the head width and the head area of the user 1 are obtained, the head volume of the user 1 can be calculated.

In addition, the bioinformation may include a body fat rate, a heart rate and/or a perspiration rate, all of which are closely related to a body density of the user. According to the head volume and the density of the user 1, a head weight of the user 1 can be obtained. The bioinformation (i.e., the density and the weight) except the head size of the user is also can be measured or sensed by an external sensor. Detailed illustration will be described hereafter.

According to the method of the present application, the nature frequency of the head of the user may be obtained on the basis of the head size (i.e., volume), density and weight of the user 1. According to the natural frequency, the playback tone of the earphone 2 can be adjusted accordingly.

Figure 4:
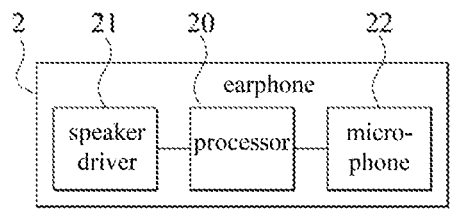
FIG. 4 is a schematic diagram according to one embodiment of the earphone of the present application.

Referring to FIG. 2 and FIG. 4, the present application further provides a tone-adjustable earphone 2. The user 1 wears the earphone 2. The earphone 2 includes a first housing 23 and a second housing 24. The first housing 23 is provided with a speaker driver 21 at the outside thereof. The second housing 24 is provided with a microphone 22 at the outside thereof. Similar to the above-mentioned, the speaker driver 21 provides a pulse signal, and the microphone 22 receives the pulse signal. The head width of the user 1 can be obtained by calculating a time difference between the pulse signal provided by the speaker driver and the pulse signal received by the microphone. The head area of the user 1 is obtained by analyzing an intensity attenuation difference between the pulse signal provided by the speaker driver and the pulse signal received by the microphone.

In an embodiment of FIG. 4, the earphone 2 includes a processor 20, such as a microprocessor, electrically connected with the speaker driver 21 and the microphone 22. Therefore, the above method may be processed through the processor 20. That is, the processor 20 calculates the head volume of the user 1 according to the time difference and the intensity attenuation difference. The processor 20 calculates a nature frequency of the head of the user 1 according to the body fat rate and the head volume of the user 1, and according to the nature frequency of the head, the processor 20 controls to adjust a playback tone of the earphone 2. For example, the user 1 inputs the body fat rate by himself or herself, or the earphone 2 is provided with a biometric sensor (not shown in the figure) to be electrically connected with the processor 20 for obtaining the bioinformation of the user 1. The body fat rate of the user 1 may be obtained by the sensor. The processor 20 calculates the nature frequency of the head of the user 1, and according to the nature frequency of the head, the processor 20 controls to adjust the playback tone of the earphone 2.

Figure 5:
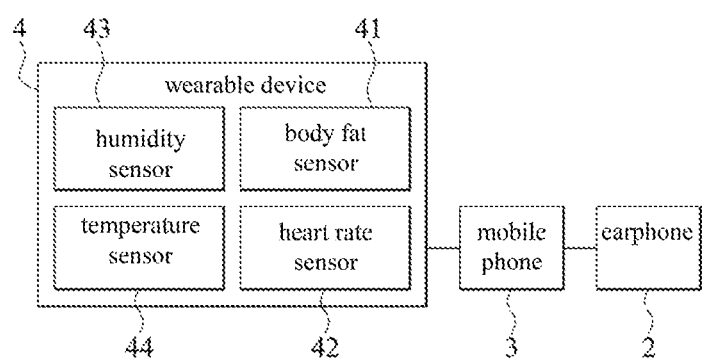
FIG. 5 is a schematic diagram showing communication between the earphone and a mobile phone according to another embodiment of the earphone of the present application.

Referring to FIG. 5, the present application further provides another tone-adjustable earphone 2. In an embodiment of FIG. 5, the earphone 2 may be communicated with a mobile phone 3. The mobile phone 3 controls a playback tone of the earphone 2. Further, the mobile phone 3 controls the earphone 2 through an application. It is known that an application can control two-way communication between the earphone 2 and the mobile phone 3, so the description is omitted herein. One objective feature of the present application is to adjust the playback tone of the earphone 2 through the application of the mobile phone 3. This will be further illustrated hereafter.

Similar to the above description, referring to FIG. 2, the user 1 wears the earphone 2. The earphone 2 includes a first housing 23 and a second housing 24. The first housing 23 is provided with a speaker driver 21 at the outside, and the second housing 24 is provided with a microphone 22 at the outside. The speaker driver 21 provides a pulse signal, and the microphone 22 receives the pulse signal.

The mobile phone 3 stores the bioinformation of the user 1, such as the bioinformation input by the user 1 himself or herself, including the body fat rate, the heart rate and/or the perspiration rate. In another embodiment, as shown in FIG. 5, the mobile phone 3 communicates with a wearable device 4. The mobile phone 3 stores the bioinformation of the user 1 recorded by the wearable device 4, including the body fat rate, the heart rate and/or the perspiration rate. In an embodiment of FIG. 5, the wearable device 4 is provided with a body fat sensor 41, a heart rate sensor 42, a humidity sensor 43 and/or a temperature sensor 44, etc. Through any one sensors or a combination thereof, the bioinformation of the user 1, including the body fat rate, the heart rate and/or the perspiration rate, etc., is obtained.

The mobile phone 3 calculates the head volume of the user 1 according to the time difference and the intensity attenuation difference, as described above. The mobile phone 3 calculates the nature frequency of the head of the user 1 according to the head volume and the body fat rate. According to the nature frequency of the head, the mobile phone 3 may further control to adjust the playback tone of the earphone 2.

Similarly, according to the intensity attenuation difference between the pulse signal provided by the speaker driver 21 and the pulse signal received by the microphone 22, the mobile phone 3 calculates the head area of the user 1. The intensity attenuation difference of the user 1 may be obtained by the acoustic shadow effect. The bioinformation includes the body fat rate, the heart rate and/or the perspiration rate. Therefore, the mobile phone 3 may calculate the head density and the head weight of the user according to the heart rate or the perspiration rate and the head volume. The nature frequency may be obtained according to the head volume, the head density and/or the head weight.

Figure 6:
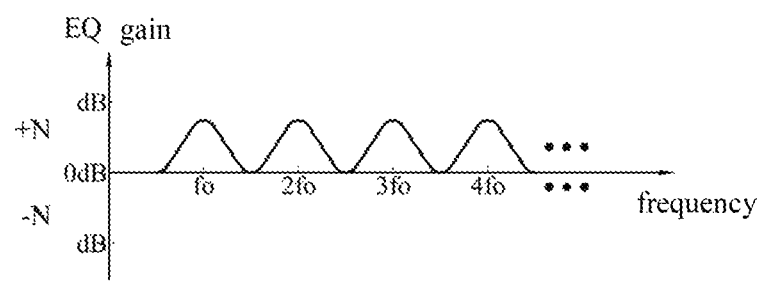
FIG. 6 is a schematic diagram of tonal balance after adjusting according to the method of adjusting a tone of the present application.

According to the present application, after the nature frequency is obtained, the playback tone of the earphone 2 may be controlled for adjustment. That is, according to the nature frequency, the playback tone may be adjusted. A parameter equalizer (PEQ) may be accompanied for adjusting tone calibration or enhancement. As shown in FIG. 6, it shows adjusting tonal balance by using acquired nature frequency f0.

Although the present application is described with reference to the above embodiments, the embodiments are not intended to limit the present application. A person of ordinary skill in the art may make variations and modifications without departing from the spirit and scope of the present application. Therefore, the protection scope of the present application should be subject to the appended claims.

What is claimed is:

1. A method of adjusting a tone when a user is wearing an earphone, the method comprising:
   obtaining bioinformation of the user, wherein the bioinformation comprises a head volume;
   calculating a nature frequency of a head of the user according to the bioinformation; and
   adjusting a playback tone of the earphone according to the nature frequency of the head.

2. The method of adjusting a tone according to claim 1, wherein the head volume of the user is obtained by utilizing a speaker driver and a microphone, the speaker driver and the microphone are respectively located at two ears of the earphone, the speaker driver provides a pulse signal, the microphone receives the pulse signal, a head width of the user is obtained by a time difference between the pulse signal provided by the speaker driver and the pulse signal received by the microphone, a head area of the user is obtained by an intensity attenuation difference between the pulse signal provided by the speaker driver and the pulse signal received by the microphone, and the head volume of the user is obtained according to the head width of the user and the head area of the user.

3. The method of adjusting a tone according to claim 2, wherein the intensity attenuation difference is based on an acoustic shadow effect of the user.

4. The method of adjusting a tone according to claim 1, wherein the bioinformation comprises a body fat rate, and a head density and a head weight of the user are obtained according to the body fat rate and the head volume.

5. The method of adjusting a tone according to claim 4, wherein the bioinformation comprises a heart rate or a perspiration rate, and the head density and the head weight of the user are obtained according to the heart rate or the perspiration rate and the head volume.

6. A tone-adjustable earphone configured to be worn by a user, the earphone comprising:
   a first housing comprising a speaker driver configured to provide a pulse signal;
   a second housing comprising a microphone, the microphone being configured to receive the pulse signal; and
   a processor electrically connected with the speaker driver and the microphone,
   wherein the processor calculates a head volume of the user according to a time difference between the pulse signal provided by the speaker driver and the pulse signal received by the microphone and according to an intensity attenuation difference between the pulse signal provided by the speaker driver and the pulse signal received by the microphone, and
   wherein the processor calculates a nature frequency of a head of the user according to a body fat rate and the head volume of the user, and according to the nature frequency of the head, the processor controls to adjust a playback tone of the earphone.

7. A mobile phone configured to communicate with a tone-adjustable earphone, wherein the mobile phone stores bioinformation of a user, the tone-adjustable earphone comprising:
   a first housing comprising a speaker driver configured to provide a pulse signal; and
   a second housing comprising a microphone, the microphone being configured to receive the pulse signal,
   wherein the mobile phone calculates a head volume of the user according to a time difference between the pulse signal provided by the speaker driver and the pulse signal received by the microphone and according to an intensity attenuation difference between the pulse signal provided by the speaker driver and the pulse signal received by the microphone, and
   wherein the bioinformation of the user comprises a body fat rate, the mobile phone calculates an nature frequency of a head of the user according to the head volume and the body fat rate, and according to the nature frequency of the head, the mobile phone controls to tune a playback tone of the earphone.

8. The mobile phone according to claim 7, wherein the intensity attenuation difference is based on an acoustic shadow effect of the user.

9. The mobile phone according to claim 7, wherein the mobile phone is communicated with a wearable device so as to obtain the bioinformation of the user, and
   the bioinformation comprises a heart rate or a perspiration rate, and a head density and a head weight of the user are calculated according to the heart rate or the perspiration rate and the head volume.

* * * * *